United States Patent
Harrewijn et al.

(10) Patent No.: US 9,510,527 B2
(45) Date of Patent: Dec. 6, 2016

(54) MALE STERILE LEEK PLANTS

(75) Inventors: Jan Leendert Harrewijn, Noord-Scharwoude (NL); Adrianus Arie Van Der Sijde, Etten-Leur (NL)

(73) Assignee: Hazera Seeds B.V. (NL)

( * ) Notice: Subject to any disclaimer, the term of this patent is extended or adjusted under 35 U.S.C. 154(b) by 1078 days.

(21) Appl. No.: 13/635,378

(22) PCT Filed: Mar. 16, 2011

(86) PCT No.: PCT/NL2011/050183
§ 371 (c)(1),
(2), (4) Date: Sep. 14, 2012

(87) PCT Pub. No.: WO2011/115486
PCT Pub. Date: Sep. 22, 2011

(65) Prior Publication Data
US 2013/0007907 A1 Jan. 3, 2013

(30) Foreign Application Priority Data
Mar. 16, 2010 (NL) .................................. 2004412

(51) Int. Cl.
- *A01H 5/00* (2006.01)
- *A01H 1/02* (2006.01)
- *A01H 1/04* (2006.01)
- *A01H 5/12* (2006.01)
- *C12Q 1/68* (2006.01)

(52) U.S. Cl.
CPC .......... *A01H 5/00* (2013.01); *A01H 1/02* (2013.01); *A01H 1/04* (2013.01); *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| WO | WO-99/23233 | 5/1999 |
|----|-------------|--------|
| WO | WO 99/23233 | * 5/1999 |

OTHER PUBLICATIONS

Engelke et al., "Mitochondrial genome variation in Allium ampeloprasum and its wild relatives," Euphytica (2004) 137:181-191.
International Search Report for PCT/NL2011/050183, mailed Jul. 11, 2011, 3 pages.
Silvertand et al., "Mannelijke steriliteit in prei (*Allium porrum* L.)," Prophyta (1989) 43(10):289-292.
Silvertand et al., "The use of male sterility in breeding of leek (*Allium ampeloprasum* L.): prospects and problems," Reproductive Biology and Plant Breeding (1992) pp. 121-122.
Silvertand, "Induction, maintenance and utilization of male sterility in leek (*Allium ampeloprasum* L.)," PhD Thesis, Dissertation; Laboratorium voor Plantenveredeling (Laboratory of Plant Breeding) (1996).

* cited by examiner

*Primary Examiner* — David T Fox
*Assistant Examiner* — Jared Shapiro
(74) *Attorney, Agent, or Firm* — McDermott Will & Emery LLP

(57) ABSTRACT

The present invention is directed to nuclear encoded dominant male sterile leek plants. A segregation for male sterility of about 50% is observed in the F1. Furthermore genetic markers linked to the nuclear encoded dominant male sterility are identified. The present invention is also directed to methods producing the nuclear encoded dominant male sterile leek plant, to methods producing hybrids from the nuclear encoded dominant male sterile leek plants, to hybrid leek plants, to seeds and parts of plants of the nuclear encoded dominant male sterile leek plants and the hybrids there from. In addition, method to use the genetic markers linked to the nuclear encoded dominant male sterile leek plants are provided.

11 Claims, No Drawings

SEQUENCE LISTING

<160> NUMBER OF SEQ ID NOS: 23

<210> SEQ ID NO 1
<211> LENGTH: 93
<212> TYPE: DNA
<213> ORGANISM: Allium porrum

<400> SEQUENCE: 1

```
ctgcagatgc gcttacgaaa acgccttctc atggcccaat gctccaacgg cgatcctatt    60
ttcgtaaaac ttacctccat cggcacctct taa                                 93
```

<210> SEQ ID NO 2
<211> LENGTH: 351
<212> TYPE: DNA
<213> ORGANISM: Allium porrum
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: misc_feature
<222> LOCATION: (293)..(294)
<223> OTHER INFORMATION: n is a, c, g, or t
<220> FEATURE:
<221> NAME/KEY: misc_feature
<222> LOCATION: (324)..(325)
<223> OTHER INFORMATION: n is a, c, g, or t

<400> SEQUENCE: 2

```
aggacgacgt tgtggagtcc ggacgatgca ttcttgtggg tggtatcsat ggagttcgcg    60
gtgatgggat tcnnnncgtg catgtgcatg gatgtgcact gattgagttt caggtggagg   120
gaaaacgtga acatgggagc ttggtaccat cggaaggggt gtgtgtatta tctgggaagg   180
gactggtaaa cacgggtgta tgtttggagg gttggcgttg atggaagtgg ctgtgttggc   240
atggaagtat ggcggtgagt ggagatatga ttggctgcgg gtgagtatac tgnnagggag   300
tcggtttggt ataaacaaag gaannaagga ctaacgaaga taagggatta a            351
```

<210> SEQ ID NO 3
<211> LENGTH: 136
<212> TYPE: DNA
<213> ORGANISM: Allium porrum
<220> FEATURE:
<221> NAME/KEY: misc_feature
<222> LOCATION: (12)..(14)
<223> OTHER INFORMATION: n is a, c, g, or t

<400> SEQUENCE: 3

```
ctgcagcgcc tnnncggtga acgccatggt ggcttcagag cttacaaggg gctacgacgt    60
cgaacatggt cgcaagcagc tcgatttggt ggtgattttg ctttagtggt ggaggaatgt   120
cattattgtc gattaa                                                   136
```

<210> SEQ ID NO 4
<211> LENGTH: 274
<212> TYPE: DNA
<213> ORGANISM: Allium porrum
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature

```
<222> LOCATION: (30)..(30)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
```

```
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t

<400> SEQUENCE: 4
ctgcagcgat gnnngagcgc angagccgtn gcgagctccg gatgagtgac gcagtgcaga      60
aactgatttg gggcagatcg atttgattcg aagaggaacn natganctgg ntgncgcgan    120
cttntggntn tctggntggg gtatgccang cgngncggnc tgtggctttc gcggctgatg    180
ganggcgcta nncgnaggan gngcnggtgg attttcncta gaggcggtgc tnttttggct    240
gaagccattt ttgacnattt tgggggaaga ttaa                                 274

<210> SEQ ID NO 5
<211> LENGTH: 343
<212> TYPE: DNA
<213> ORGANISM: Allium porrum

<400> SEQUENCE: 5
ctgcagcgtt gggtgcatgg ttggcgatag gagtgtggta tggtgttcac gacaatggag      60
ttgctgttat gggactggga ggtgaacagg ccgcatggta ctgtgcattt gcgaaacaat    120
gaaggtaatg ggctgtttct ttttttctgg aacatattac ttgcgttggt gacagaagtt    180
gttttactga gggtgatcac gaggggaaga ggatgcgagg tggagctgag tagtagcaag    240
tggacggtat ggttcagacg ggaagaaaac aacataaata gagaagagaa ataaggaaga    300
tgggctagaa ttttcataag gggcctgggc ctaagcgctt taa                      343

<210> SEQ ID NO 6
<211> LENGTH: 154
<212> TYPE: DNA
<213> ORGANISM: Allium porrum

<400> SEQUENCE: 6
tgcagccaat agtcgagcag cttccttcca ccgttcccct catcaaggca ctaccacaca      60
ttgccaacat cctaaccact cagtgatcac cgccgcatgt ccttcgcaga cccccttacc    120
cctatagtaa actaaacatg ccactccaca ttaa                                 154

<210> SEQ ID NO 7
<211> LENGTH: 18
<212> TYPE: DNA
<213> ORGANISM: Artificial
<220> FEATURE:
<223> OTHER INFORMATION: AFLP marker

<400> SEQUENCE: 7
gactgcgtac atgcagcg                                                    18

<210> SEQ ID NO 8
<211> LENGTH: 18
<212> TYPE: DNA
<213> ORGANISM: Artificial
<220> FEATURE:
<223> OTHER INFORMATION: AFLP marker

<400> SEQUENCE: 8
```

-continued gactgcgtac atgcagat         18

<210> SEQ ID NO 9
<211> LENGTH: 18
<212> TYPE: DNA
<213> ORGANISM: Artificial
<220> FEATURE:
<223> OTHER INFORMATION: AFLP marker

<400> SEQUENCE: 9
gactgcgtac atgcagaa         18

<210> SEQ ID NO 10
<211> LENGTH: 18
<212> TYPE: DNA
<213> ORGANISM: Artificial
<220> FEATURE:
<223> OTHER INFORMATION: AFLP marker

<400> SEQUENCE: 10
gactgcgtac atgcagcc         18

<210> SEQ ID NO 11
<211> LENGTH: 19
<212> TYPE: DNA
<213> ORGANISM: Artificial
<220> FEATURE:
<223> OTHER INFORMATION: AFLP marker

<400> SEQUENCE: 11
gatgagtcct gagtaaagc         19

<210> SEQ ID NO 12
<211> LENGTH: 19
<212> TYPE: DNA
<213> ORGANISM: Artificial
<220> FEATURE:
<223> OTHER INFORMATION: AFLP marker

<400> SEQUENCE: 12
gatgagtcct gagtaatgg         19

<210> SEQ ID NO 13
<211> LENGTH: 19
<212> TYPE: DNA
<213> ORGANISM: Artificial
<220> FEATURE:
<223> OTHER INFORMATION: AFLP marker

<400> SEQUENCE: 13
gatgagtcct gagtaaatc         19

<210> SEQ ID NO 14
<211> LENGTH: 19
<212> TYPE: DNA
<213> ORGANISM: Artificial
<220> FEATURE:
<223> OTHER INFORMATION: AFLP marker

<400> SEQUENCE: 14
gatgagtcct gagtaatcg         19

<210> SEQ ID NO 15
<211> LENGTH: 19
<212> TYPE: DNA

```
<213> ORGANISM: Artificial
<220> FEATURE:
<223> OTHER INFORMATION: AFLP marker

<400> SEQUENCE: 15
gatgagtcct gagtaaaag                                               19

<210> SEQ ID NO 16
<211> LENGTH: 19
<212> TYPE: DNA
<213> ORGANISM: Artificial
<220> FEATURE:
<223> OTHER INFORMATION: AFLP marker

<400> SEQUENCE: 16
gatgagtcct gagtaagag                                               19

<210> SEQ ID NO 17
<211> LENGTH: 19
<212> TYPE: DNA
<213> ORGANISM: Artificial
<220> FEATURE:
<223> OTHER INFORMATION: AFLP marker

<400> SEQUENCE: 17
gatgagtcct gagtaatcc                                               19

<210> SEQ ID NO 18
<211> LENGTH: 19
<212> TYPE: DNA
<213> ORGANISM: Artificial
<220> FEATURE:
<223> OTHER INFORMATION: AFLP marker

<400> SEQUENCE: 18
gatgagtcct gagtaatct                                               19

<210> SEQ ID NO 19
<211> LENGTH: 19
<212> TYPE: DNA
<213> ORGANISM: Artificial
<220> FEATURE:
<223> OTHER INFORMATION: AFLP marker

<400> SEQUENCE: 19
gatgagtcct gagtaatgt                                               19

<210> SEQ ID NO 20
<211> LENGTH: 21
<212> TYPE: DNA
<213> ORGANISM: Artificial
<220> FEATURE:
<223> OTHER INFORMATION: adapter alpha

<400> SEQUENCE: 20
ctcgtagact gcgtacatgc a                                            21

<210> SEQ ID NO 21
<211> LENGTH: 15
<212> TYPE: DNA
<213> ORGANISM: Artificial
<220> FEATURE:
<223> OTHER INFORMATION: adapter beta

<400> SEQUENCE: 21
gacgatgagt cctga                                                   15
```

```
<210> SEQ ID NO 22
<211> LENGTH: 14
<212> TYPE: DNA
<213> ORGANISM: Artificial
<220> FEATURE:
<223> OTHER INFORMATION: adapter

<400> SEQUENCE: 22
tgtacgcagt ctac                                                       14

<210> SEQ ID NO 23
<211> LENGTH: 14
<212> TYPE: DNA
<213> ORGANISM: Artificial
<220> FEATURE:
<223> OTHER INFORMATION: adapter

<400> SEQUENCE: 23
tactcaggac tcat                                                       14
```

MALE STERILE LEEK PLANTS

CROSS-REFERENCE TO RELATED APPLICATIONS

This application is the national phase of PCT application PCT/NL2011/050183 having an international filing date of 16 Mar. 2011, which claims benefit of Netherlandic patent application No. 2004412 filed 16 Mar. 2010. The contents of the above patent applications are incorporated by reference herein in their entirety.

SEQUENCE LISTING

The instant application contains a Sequence Listing which has been submitted in ASCII format via EFS-Web and is hereby incorporated by reference in its entirety. Said ASCII copy is named P90781US00 seqlist_ST25.txt and is 8,000 bytes in size.

The present invention relates to nuclear encoded dominant male sterile leek plants and to genetic markers identifying the nuclear encoded dominant male sterile trait in leek plants. In addition methods are provided to produce nuclear encoded dominant male sterile leek plants, to produce hybrid leek plants, and produce a nuclear encoded dominant male sterile leek line.

BACKGROUND

Leek (*Allium ampeloprasum*) belongs to the Alliaceae family. It is used as a vegetable and is grown worldwide, and in Europe it is an important commercial crop. Several factors make leek a difficult crop to improve (review Currah 1986). First it is a biannual crop, which means that in the first year the plant develops and after vernalisation in the winter it will flower in the second year.

Leek is also subject to severe inbreeding depression. The frequency of recessive lethal and deleterious genes is high. Already after one generation of selfing severe losses of vigor and seed production can be observed (Schweisguth 1970). As a consequence of the inbreeding depression, positive mass selection has been the most important way of improvement. Leek is an outbreeding species, but self-pollination does occur and frequencies up to 20% have been found in commercial cultivars (Beringer and Buret 1967). The open pollinated cultivars are highly heterogeneous. One of the factors contributing to this high heterogeneity is this high percentage of selfing, which results in inbreeding depression.

The cultivated leek is tetraploid (2n=4x=32), which makes breeding complicated. Most authors agree that leek is an autotetraploid, because for most of the genes leek shows tetrasomic inheritance (Schweisguth 1970, Beringer and Buret 1967). Objectives for leek breeding include improvement of winter-hardiness, a long shaft length, absence of bulbing, resistance to bolting, upright habitat, dark-green leaves and easy to peel. In addition to these improvements in quality, breeders also aim for improvement in yield, uniformity and resistance to pests and diseases.

Nowadays most breeding programs develop F1 hybrid cultivars, which have considerable benefits with regard to open-pollinated (OP) cultivars used before. Advantages of production of F1 hybrids are improvement of uniformity of the crop and better exploitation of heterosis for several traits, i.e. yield and faster fixation of desirable traits. Schweisguth (1970) has demonstrated heterosis in leek by making experimental hybrids between inbreds. These hybrids gave yields greater than the best open-pollinated cultivar and were more uniform.

To maintain the uniformity of the crop, prevention of selfing in hybrid seed production is needed. For some crops the selfing may be prevented by emasculation of the flowers, like is done for tomato and sweet pepper. In normal leek plants, however, the flowers are very small and there are many flowers on one flower head, which makes it impossible to emasculate by hand. Therefore, for the production of hybrids in leek it is advantageous to use plants that are male sterile.

Plants can be made sterile by genetic modification (GM). WO99/23233; Mogen Int. describes the production of male sterile plants by introducing recombinant DNA expressing trehalose phosphate phosphatase (TPP) in the plant. From the examples it can be seen that when the plant is transgenic for the TPP gene, it displays a male sterile phenotype. Tobacco, lettuce, and Arabidopsis are transformed with TPP. No examples in leek are given. In many countries, including most European countries, GM plants are not allowed and thus plants that are male sterile by transformation are not accepted in these countries.

Male sterility may be obtained by a non-GM route. One system for male sterility is based on cytoplasmic male sterility, like used in onions (*Allium cepa*). Many experiments and projects have been done to find or introduce this kind of male sterility into leek (Silvertand 1995, Buitenveld 1998). Some have been trying to introduce cytoplasm from other species like onion or *Allium galanthum* by conventional crossing or somatic hybridization. In WO2010/007059 cytoplasmic male sterility from garlic (*Allium sativum*) was introduced in leek plants. However, cytoplasmic male sterility (CMS) has a number of disadvantages including increased disease susceptibility, breakdown of sterility under certain conditions, the need to develop a set of CMS- and maintainer lines that are genetically the same, except for the cytoplasm (isogenic lines). This is necessary to multiply the CMS-line by seed. The expression of CMS can be complicated by the presence of restorer genes in the nucleus. Restorer genes are genes that can suppress the male sterile effect of the cytoplasm and are incorporated into the male parent to restore pollen fertility. Good maintainer lines need to be developed without restorer genes. In case of tetraploid inheritance in leek this is a complicated task, which can only be achieved by inbreeding the maintainer lines and selecting the ones without restorer. Inbreeding may then lead to strong inbreeding depression. When restorer genes are introduced, they may be linked to undesirable traits.

Another system for male sterility is nuclear encoded male sterility (NMS). This male sterility is controlled by nuclear genes. For NMS it is impossible to develop an isogenic set of NMS-line and maintainer line to multiply the NMS-line by seed, because the offspring of the NMS-line will always segregate for sterility. This means that the male sterile parent must be maintained vegetatively. This is now possible by using tissue culture or bulbils (little bulbs) produced in the flower head (Silvertand 1995). The progeny is a clone of the original sterile plant and shows the same traits. For NMS there is no need for development of sets of NMS- and maintainer lines, in contrast to CMS.

The nuclear male sterility as currently being used in modern hybrids has most likely a recessive nature. The assumption has been made that one or two recessive genes are responsible for the male sterility trait. Silvertand (1996)

reports a percentage of 0.4% of naturally occurring male sterile plants, found after screening open pollinated seed productions in Italy.

If one wants to introduce recessive male sterility in another desired leek plant one has to cross the desired leek plant with a source for genetic male sterility. The heterozygous F1-generation produced there from has to be selfed and in the F2-generation a segregation for male sterility can be found. Assuming 1 recessive gene (ms), 1/36 of the F2-population shows the desired trait (Briggs & Knowles, 1967).

In a biannual crop like leek, one generation of backcrossing with a recessive male sterility trait costs 4 years: one generation of 2 years to make a cross between a sterile and fertile plant. The F1 plants are all fertile as the sterility is recessive in this case. Therefore another crossing step is needed which is often the selfing of the F1 to produce an F2, which takes another 2 years for a biannual crop. The F2 generation has to be grown until flowering because the distinction between male fertile and male sterile cannot be made until flowering. In the F2 generation a high amount of plants must be checked in order to find a male sterile plant because only 1/36=3% is sterile. If one also wants to have the possibility to select between male sterile plants to find a better plant with other desired traits, the F2 population has to be even bigger. The second cycle of backcross takes again 4 years because there will be no male sterile plants in the F1 because of the recessive nature of the male sterility trait. In order to convert a male fertile line into a similar male sterile line about 5 backcrosses are needed in a conventional backcross programs. This will take about 20 years for a tetraploid breeding crop like leek with a recessive male sterility trait.

It would be advantageous to have a dominant male sterility trait, because the male sterility trait would already appear in the F1 generation. This would reduce the stabile conversion into a male sterile line to about 10 years, instead of 20. In addition, for a dominant male sterile trait, in the F1 generation about 50% of the plants would be male sterile, instead of only 3% in the F2 generation of recessive male sterility. However, in order to maintain male sterility human intervention is required.

It is therefore an object of the present invention to provide a leek plant that possesses a dominant male sterility trait. Another object of the present invention is to identify genetic markers that are linked to this dominant male sterility trait. Yet another object of the present invention is to make hybrid leek plants and seeds with the dominant male sterility trait. In addition another object of the invention is to provide a method for selecting for dominant male sterile leek plants by using the genetic markers, as well as leek producing method using selection based on the genetic markers for dominant sterility.

One or more of these objectives are met by the present invention. The present invention provides a nuclear encoded male sterile leek plant wherein the male sterility trait is dominant. These male sterile leek plants produce about 50% male sterile F1 offspring. The male sterile leek plants of the present invention are used to produce F1 hybrid leek plant seeds. The seeds from the dominant male sterile leek plant are deposited at NCIMB Ltd, Aberdeen under number NCIMB 41699.

In addition, the present invention provides genetic markers that are linked to the dominant male sterility trait. Furthermore methods are provided to use the genetic marker in selection for male sterile leek plants.

DETAILED DESCRIPTION

The present invention provides a nuclear encoded male sterile leek plant wherein the male sterility trait is dominant. Male sterility indicates that a plant has no fertile pollen and because of this, male sterile plants are incapable of self pollination. Dominant male sterility in the present invention indicates that a large portion of the F1 offspring is male sterile. Preferably about 10% to about 80% of a F1 offspring is male sterile, more preferably about 20 to about 70% is male sterile, even more preferably about 40 to about 50% is male sterile.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes, in a tetraploid organism such as leek, four alleles do this.

A "gene" is defined herein as a hereditary unit consisting of a sequence of DNA that occupies a specific location on a chromosome and that contains the genetic instruction for a particular characteristic or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "nuclear" means originating from the nucleus. Nuclear sterility means that the sterile trait originates from the nucleus.

As used herein, the term "cytoplasmic" means originating from the cytoplasm. Cytoplasmic sterility means that the sterile trait originates from the cytoplasm.

As used herein "genic" means originating from genes, it comprises both nuclear and extranuclear. Mitochondria also contain genes, but are extranuclear organelles.

As used herein "dominant" means the relationship between two or more variant forms (alleles) of a single gene, in which one allele masks the expression of the other in influencing some trait. In the simplest case, if a gene exists in two allelic forms (A & B), three combinations of alleles (genotypes) are possible: AA, AB, and BB. If AB individuals (heterozygotes) show the same form of the trait (phenotype) as AA individuals (homozygotes), and BB homozygotes show an alternative phenotype, allele A is said to dominate or be dominant to allele B, and B is said to be recessive to A.

As used herein, the term "offspring" means any product of a cross between individuals. Offspring includes but is not limited to seed and/or, plant. In the present invention bulbil and basal bulb may also be considered off-spring although strictly speaking they are a clone of a individual plant and not the production of a cross.

As used herein, the term "selfing" means a cross between genetically like individuals, often between individuals of the same offspring.

As used herein, the term "hybrid" means any offspring of a cross between two genetically unlike individuals.

As used herein, the term "inbred" or "line" means a substantially homozygous individual.

In this application a "recombination event" is understood to mean a meiotic crossing-over.

As used herein, the terms "introgression", "introgressed" and "introgressing" refer to both a natural and artificial process whereby genes of one species, variety or cultivar are moved intra- or interspecifically into the genome of species, variety or cultivar or line, by crossing. The process may optionally be completed by backcrossing to the recurrent parent.

"Genetic engineering", "transformation" and "genetic modification" are all used herein as synonyms for the transfer of isolated and cloned genes into the DNA, usually the chromosomal DNA or genome, of another organism.

As used herein, the term "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers Random Amplification of Polymorphic DNA (RAPD) profile, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a nucleic acid sequence present on the genome.

As used herein GM plants are genetically modified plants and are plants whose DNA is modified using genetic engineering techniques. In most cases the aim is to introduce a new trait to the plant which does not occur naturally in the species. Examples include resistance to certain pests, diseases or environmental conditions, or the production of a certain nutrient or pharmaceutical agent. Genetic engineering involves the use of recombinant DNA techniques, but does not include traditional animal and plant breeding or mutagenesis, such as treating seeds or plant part with a mutagens.

As used herein, the term "plant part" indicates a part of the leek plant, including single cells and cell tissues such as plant cells that are intact in plants, cell clumps and tissue cultures from which leek plants can be regenerated. Examples of plant parts include, but are not limited to, single cells and tissues from pollen, ovules, leaves, embryos, roots, root tips, anthers, flowers, shaft, and seeds, seed coat, as well, protoplasts, calli, and the like.

As used herein, the term "population" means a genetically heterogeneous collection of plants sharing a common genetic derivation.

As used herein, the term "leek" means any plant, line or population known under the species name of *Allium ampeloprasum* or *Allium porrum*. Varieties or cultivars including but not limited to Bulgaarse reuzen, Duraton, Julita, Krypton, WR1GOLD-92035V, Alita, Alma, Antiope, Antlia, Apollo, AR-954616, Aries, Artemis, Ashton, Bell, Belton, Bluebell, Bluetan, Breugel, Cadet, Carentan 2, Carlton, Carver, Casino, Castan, Catcher, Centaurus, Cezanne, Chardin, Christiane, Coolidge, Cottrell, Cousteau, Darwin, Davinci, Delmas, Delvaux, Dinton, Dionysos, Drayton, Dumas, Easton, Edison, Einstein, Europa, Fahrenheit, Fleming, Flextan, Galvani, Gavia, Goltan, Goya, Harston, Helios, Herakles, Jolant, Julian, Jumper, Kenton, King Shaft, Kingpin, Kingston, Krystina, Lampton, Lawrence, Leroy, Levis, Lexton, Linx, Logan, Longton, Malouda, Manet, Marshal, Matejko, Megaton, Mendel, Midfield, Miracle, Moreton, Morse, MS-954598, Natan, Newton, Nipkow, Nobel, Norton, NUN7001LE, NUN7011LE, NUN7021LE, NUN7031LE, NUN7041LE, Oarsman, Oceanos, Oktan, Pallas, Pancho, Parker, Parton, Pasteur, Perec, Pixton, Porridor, Poulton, PR6220RXZ, PR6440 RZ, Pretan, Previta, Princeton, Raytan, Rentan, Robique, Rolan, Roxton, Rubens, Ruisdael, Runner, Saxton, SENG 9167, Seng 9172, SENG 9174, Servaes, Shelton, Spartan, Sprintan, Stanley, Stanton, Striker, Siltan, Surfer, Surprise, Triton, Upton, Vangogh, Vitalon, Viton, Volta, Walton, Winterreuzen 2, WR 1, WR1KAZ-92010V, Wright, Yutan, Zenthos, Zeus.

As used herein, the term "variety" or "cultivar" means a group of similar plants that by structural or genetic features and/or performance can be distinguished from other varieties within the same species.

A "cultivated plant" is defined herein as a plant exhibiting agronomically desirable characteristics. The term is used in contrast to the term "wild", which indicates a variety that is of no immediate commercial interest due to undesirable traits.

The term "male sterile" is used herein in its art-recognized meaning. Male sterile means the inability to form viable seeds. This may be due to the absence of viable pollen or when the pollen is viable but it cannot reach the pistil due to some morphological deviation of the flowers. Male sterile also includes the possibility that seed is produced, but the seed is of poor capability and is unable to produce plants. Male sterility may also include the possibility that viable seed or embryos are produced, but that due to some morphological deviation or other circumstances, the seed or embryo cannot be liberated by the plant germinate by itself and it needs human intervention to germinate or liberate the seed or embryo.

Hybrids are the product of a cross between genetically unlike parents. The development of hybrids in a plant breeding program requires, in general, the development of homozygous inbred lines, the crossing of these lines, and the evaluation of the crosses. Most plant breeding programs combine the genetic backgrounds from two or more inbred lines or various other broad-based sources into breeding pools from which new inbred lines are developed by selfing and selection of desired phenotypes. Hybrids can also be used as a source of plant breeding material or as source populations from which to develop or derive new plant lines. The expression of a trait in a hybrid may exceed the midpoint of the amount expressed by the two parents, which is known as hybrid vigor.

Inbred lines may for instance be derived from hybrids by using said methods as pedigree breeding and recurrent selection breeding. Newly developed inbreds are crossed with other inbred lines and the hybrids from these crosses are evaluated to determine which of those have commercial potential.

Pedigree breeding is a system of breeding in which individual plants are selected in the segregating generations from a cross on the basis of their desirability judged individually and on the basis of a pedigree record.

Recurrent selection is a breeding method based upon intercrossing selected individuals followed by continuing cycles of selection and intercrossing to increase the frequency of desired alleles in the population.

Recurrent selection may for instance be performed by backcross breeding, which involves a system of breeding whereby recurrent backcrosses are made to one of the parents of a hybrid, accompanied by selection for a specific character or characters.

The backcross being the cross of a hybrid to either of its parents. Backcrossing can for instance be used to transfer a specific desirable trait that is present in a donor plant line to another, superior plant line (e.g. an inbred line) that lacks that trait. The first step of this process involves crossing the superior plant line (recurrent parent) to a donor plant line (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait and for the germplasm inherited from the recurrent parent, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

A general description of breeding methods commonly used for acquiring different traits in various crops, including leek, can be found in reference books such as e.g., Allard, R. W. (1960) *Principles of Plant Breeding*; Simmonds, N. W. (1979) *Principles of Crop Improvement*; Mark J. Basset, (1986, editor), *Plant Breeding Perspectives*; Fehr, (1987) *Principles of Cultivar Development Theory and Technique*), Curah L (1986) *Leek breeding: a review* J Hort Sc 61: 407-415

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

Half-sib family: offspring of one mother plant that has been fertilized by more than one father plant either intentionally, or by open pollination.

Bulbils are small bulbs which occur in the flower head, when the flowers fade, are removed or even instead of flowers. It occurs in several members of the family Alliaceae. The bulbils are a convenient way to maintain a male sterile plant vegetatively. The bulbils are removed and transferred to growth medium such as soil and can be grown into a plant.

A bulblet or basal bulb (Dutch: klister) is a little bulb formed underground as a reproductive structure, also seen in other bulb crops like lily, tulip and onion. It can be harvested after flowering and is another good method to maintain the genotype vegetatively.

As used herein, resistance of diseases is as defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of a plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art.

The present invention is directed to a male sterile leek plant wherein the male sterility is dominant and nuclear encoded. Preferably the male sterile leek plant is obtainable from seed as deposited at the NCIMB with deposit number NCIMB 41699. In a preferred embodiment the male sterile leek plant has offspring wherein about 10% to about 80% of the leek plants are male sterile, preferably about 30% to about 60%, or more preferably about 40% to about 50%. The dominant trait makes that the F1 offspring already segregates for male sterility. This is in contrast to recessives male sterility, wherein the F1 are all fertile and only after selfing the heterozygous F1, a small portion (+/−3%) of the F2 is male sterile. The segregation for male sterility already in the F1 and with at least 10% or even more of the F1 being male sterile offers huge advantages in breeding programs.

In a preferred embodiment male sterile leek plant according to the invention is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148.

The AFLP markers consist of a forward primer and a reverse primer. When a PCR is performed a fragment with a specific size is obtained, see table 4. Six of these specific fragments were sequenced and are represented in SEQ ID NO 1-6. A person skilled in the art may design any kind of genetic marker protocol to indicate the presence of the sequences in the DNA of a leek plant. Examples of such genetic marker protocol include but are not limited to restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers, Sequence Tagged site (STS) markers or isozyme markers or combinations of the markers described herein which defines a nucleic acid sequence present on the genome. The skilled person may design suitable PCR primers to detect the presence of the nucleic acid sequence SEQ ID NO 1-6 in the genome. All these experiments are well within the skill of a skilled person.

In addition, homologues of SEQ ID NO 1-6 may also be used. Preferably the homologues are at least 70%, more preferably at least 80% and most preferably at least 90%, or even 95% or 98% homologous. Preferably the homologues contain no more than 10 nucleotides mismatch, more preferably no more than 7 nucleic acid mismatch, even more preferably no more than 5 nucleotides mismatch. Most preferably no more than 2 nucleotides mismatch. Sequence homology can be determined by any suitable sequence alignment method, e.g. BLAST.

In a preferred embodiment male sterile leek plant according to the invention comprise a genetic marker that is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In another preferred embodiment, the male sterile leek plant according to the invention is not a GM plant. Preferably the male sterile leek plant according to the present invention is not produced by a genetic engineering technique. Preferably the male sterile leek plant of the present invention is produced by conventional breeding techniques, preferably in combination with mutagenesis, preferably treating the seeds with a mutagens.

In a preferred embodiment male sterile leek plant according the invention have a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, *Phythophthora* spp., *Cladosporium* spp., *Alternaria* spp., *Stemphylium* spp., thrips, *Pseudomonas* spp.

In another preferred embodiment the shaft length is at least 25 cm, more preferably at least 30 cm.

The erectness is measured as the angle between the basis of the leaf relative to the shaft axis at maturity. An erectness of 0° is when the leaf is straight up, in the line of the shaft. An erectness of 90° indicates that the leaf is perpendicular to the shaft. Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention has an erectness of the leaves of less than 50°, more preferably less than 45°, and even more preferably less than 40°. In a preferred embodiment, more than 80% of the leaves have an erectness of less than 50°, more preferably less than 45° and most preferably less than 40°. Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Bulbing of the shaft is when the bottom part at the foot of the shaft has a larger diameter than the upper part of the shaft near the leaves of the leek plant. In the present invention, no bulbing of the shaft means that the bottom part of the shaft has a diameter that is less than 30% larger than the diameter of the upper part of the shaft, more preferably less than 20% larger than the upper part of the shaft, and most preferably less than 15% larger than the upper part of the shaft.

In a preferred embodiment male sterile leek plant according to the present invention the nuclear encoded dominant male sterile leek plant is propagated vegetatively.

Nuclear encoded dominant male sterile leek plant are suitably propagated vegetatively. Plants may be regenerated from cells or tissue or organs of leek through various procedures including but not limited to doubled haploidisation, somatic hybridization, protoplast fusion, genetic transformation, vegetative propagation using leek cells, pollen, protoplasts, suspension cultures, callus, basal plates, flower heads, ovules, (somatic) embryos, leaves, roots and other plant parts using previously described methods such as described in Schavemaker C M, Jacobsen E (1995) Development of a cyclic somatic embryogenesis regeneration system for leek (*Allium ampeloprasum* L.) using zygotic embryos. Plant Cell Reports 14: 227-231. Buiteveld J, Valk van der P, Jansen J, Creemers-Molenaar J, Colijn-Hooymans C M (1993) Callus induction and plant regeneration from explants of commercial cultivars of leek (*Allium ampeloprasum* var. *porrum* L.). Plant Cell Reports 12: 431-434. Buiteveld J, Suo Y, Lookeren Campagne van M M, Creemers-Molenaar J (1998) Production and characterization of somatic hybrid plants between leek (*Allium ampeloprasum* L.) and onion (*Allium cepa* L.) Theoretical and Applied Genetics 96, 765-775. Novak FJ (1986) *Allium*. In: Evans DA Handbook of plant cell culture 4, New York, pp 419-456.

In another embodiment the present invention is directed to a method of producing a hybrid leek plant seed that comprise nuclear encoded male sterility comprising the steps of:
(a) Providing a first leek plant that is nuclear encoded dominant male sterile
(b) Providing a second leek plant that is fertile
(c) Crossing the first and second leek plant to produce offspring In another embodiment the present invention is directed to a method of providing a nuclear encoded dominant male sterile leek plant comprising the steps of:
(a) Providing a first leek plant that is nuclear encoded dominant male sterile
(b) Providing a second leek plant that is male fertile
(c) Crossing the first and second leek plant to produce offspring In another embodiment the present invention is directed to a method of providing a nuclear encoded dominant male sterile three way hybrid leek plant or seed comprising the steps of:
(a) Providing a first leek plant that is nuclear encoded dominant male sterile
(b) Providing a second leek plant that is male fertile
(c) Crossing the first and second leek plant to produce offspring
(d) Selecting for a leek plant in the offspring of step (c) that is nuclear encoded dominant male sterile.
(e) Providing a third leek plant that is male fertile
(f) Crossing the selected nuclear encoded dominant male sterile leek plant from step (d) with the third leek plant to produce offspring In another embodiment the present invention is directed to a method of introgressing an allele encoding nuclear encoded dominant male sterility into a leek plant comprising:
(a) Providing a first leek plant that is nuclear encoded dominant male sterile
(b) Providing a second leek plant that is male fertile
(c) Crossing the first and second leek plant to produce offspring In a preferred embodiment the method according to the present invention comprises the steps of:
(e) crossing of a leekplant from step (c) and a leekplant from step (b) to produce offspring
(f) repeating step (d) and (e) one, two, three, or four times.

In a preferred embodiment of the present invention the nuclear encoded dominant male sterility trait is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

In a preferred embodiment the method according to the present invention comprises a step for selection for nuclear encoded dominant male sterility in seed or leek plants from offspring. Preferably the method according to the presenting invention comprises at least one marker assisted selection step. Preferably the first nuclear encoded dominant male sterile leek plant is selected by marker assisted selection step for nuclear encoded dominant male sterility. Suitably the step for selection for seeds or leek plants from offspring comprises a marker assisted selection step for nuclear encoded dominant male sterility. Suitably the marker assisted selection step is carried out with at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

In a preferred embodiment a method according to the present invention the leek plant or seed that is nuclear encoded dominant male sterile or the leek plant or seed that has the nuclear encoded dominant male sterility trait is propagated vegetatively.

Nuclear encoded dominant male sterile leek plant according to the present invention are suitably propagated vegetatively. Plants may be regenerated from cells or tissue or organs of leek through various procedures including but not limited to doubled haploidisation, somatic hybridization, protoplast fusion, genetic transformation, vegetative propagation using leek cells, pollen, protoplasts, suspension cultures, callus, basal plates, flower heads, ovules, (somatic) embryos, leaves, roots and other plant parts using previously described methods.

In a preferred embodiment in the method according to any the present invention the leek plant or seed that is nuclear encoded dominant male sterile or the leek plant or seed that has the nuclear encoded dominant male sterility trait is obtainable from seed as deposited at the NCIMB with deposit number NCIMB 41699.

In a preferred embodiment in the method of the present invention the offspring of the male sterile leek plant or seed is about 10% to about 80% male sterile, preferably about 30% to about 60%, or more preferably about 40% to about 50%.

In a preferred embodiment in the method according to the present invention, the leek plant or seed that is nuclear encoded dominant male sterile or the leek plant or seed that has the nuclear encoded dominant male sterility trait is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

In another preferred embodiment the method according to the present invention the leek plant or seed that is nuclear encoded dominant male sterile or the leek plant or seed that has the nuclear encoded dominant male sterility trait has a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, *Phythophthora* spp., *Cladosporium* spp., *Alternaria* spp., *Stemphylium* spp., thrips, *Pseudomonas* spp. Preferably the shaft length is at least 25 cm, more preferably at least 30 cm.

Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention has an erectness of the leaves of less than 50°, more preferably less than 45°, and even more preferably less than 40°. In a preferred embodiment, more than 80% of the leaves have an erectness of less than 50°, more preferably less than 45° and most preferably less than 40°. Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Preferably the bottom part of the shaft has a diameter that is less than 30% larger than the diameter of the upper part of the shaft, more preferably less than 20% larger than the upper part of the shaft, and most preferably less than 15% larger than the upper part of the shaft.

Another embodiment of the present invention is directed to a method to grow a nuclear encoded dominant male sterile leek plant by somatic reproduction from a tissue, cell or protoplast derived from a nuclear encoded dominant male sterile leek plant or seed according to the invention or obtainable from a method according to the invention.

In addition, the present invention is directed to a method of providing a bulbil from nuclear encoded dominant male sterile leek plant comprising the steps of:
 (a) Providing a first nuclear encoded dominant male sterile leek plant
 (b) Growing the first nuclear encoded dominant male sterile leek plant from step (a) until flowering
 (c) Removing at least 25% of the number of flowers from the flower head of the nuclear encoded dominant male sterile leek plant from step (b)
 (d) Repeating step (c) until a bulbil is grown
 (e) Harvesting the bulbil from leek plant More preferably removing at least 40%, or even at least 50%, even more preferably removing at least 75% of the number of flowers from the flower head or most preferably removing all the flowers from the flower head. Preferably the first nuclear encoded dominant male sterile leek plant is selected by marker assisted selection step for nuclear encoded dominant male sterility.

The present invention is also directed to a method of vegetatively propagating a nuclear encoded dominant male sterile leek plant comprising the steps of:
 (a) Providing a nuclear encoded dominant male sterile bulbil according to the invention
 (b) Transferring the bulbil to a growth medium
 (c) Allowing the bulbil to grow into a plant Preferably the plant or bulbil obtained from the method according to the present invention is checked for the nuclear encoded dominant male sterility by checking the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

Preferably the leek plant or seed that is nuclear encoded dominant male is obtainable from seed as deposited at the NCIMB with deposit number NCIMB 41699. More preferably the plant or seed obtained from the method according to the present invention has a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, *Phythophthora* spp., *Cladosporium* spp., *Alternaria* spp., *Stemphylium* spp., thrips, *Pseudomonas* spp. Preferably the shaft length is at least 25 cm, more preferably at least 30 cm.

Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention have an erectness of the leaves of less than 50°, more preferably less than 45°, and even more preferably less than 40°. In a preferred embodiment, more than 80% of the leaves have an erectness of less than 50°, more preferably less than 45° and most preferably less than 40°. Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Preferably the bottom part of the shaft has a diameter that is less than 30% larger than the diameter of the upper part of the shaft, more preferably less than 20% larger than the upper part of the shaft, and most preferably less than 15% larger than the upper part of the shaft.

The present invention is also directed to nuclear encoded dominant male sterile seed or plant obtainable from a method according to the present invention, and to nuclear encoded dominant male sterile leek plant obtainable from growing the seed according to the present invention.

Furthermore, the present invention is directed to plant part derived from a nuclear encoded dominant male sterile leek plants or seed or bulbil according to the present invention, or obtainable from a method according to the present invention wherein the plant part is selected from the group consisting of leaf, pollen, ovule, embryo, root tip, anthers, flowers, seed, seed coat, stem, bulbil, basal bulb or tissue of any thereof.

More over, the present invention is directed to a regenerable cell or protoplast derived from a nuclear encoded dominant male sterile leek plant or seed or bulbil according to the present invention or obtainable from a method according the present invention, wherein the cell or protoplast regenerates to a leek plant being nuclear encoded dominant male sterile, preferably the cell or protoplast is from a tissue selected from the group consisting of leaf, pollen, ovule, embryo, root tip, anthers, flowers, seeds, seed coat, stem, bulbil, basal bulb.

The present invention is furthermore directed to a nuclear encoded dominant male sterile leek plant regenerated from the cell or protoplast or plant part according to the present invention. Preferably the nuclear encoded dominant male sterile bulbil is obtainable from the method according to the present invention.

In a preferred embodiment the present invention is directed to a nuclear encoded dominant male sterile leek plant obtainable from a bulbil according to the present invention.

A nuclear encoded dominant male sterile leek plant according to the present invention is suitably obtained from bulbil. The bulbil may be obtained from flower heads of leek of which at least part of the flowers are repeatedly removed. The bulbil may be removed from the flower head and transferred to an appropriate growth medium to be grown into a plant.

Preferably, nuclear encoded dominant male sterile seed or plant, plant part, bulbil regenerable cell, or protoplast according to the present invention have offspring wherein the leek plants are about 10% to about 80% male sterile, preferably about 30% to about 60%, or more preferably about 40% to about 50%.

Preferably the nuclear encoded dominant male sterile seed or plant, plant part, bulbil regenerable cell, or protoplast according to the present invention is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

Preferably, the nuclear encoded dominant male sterile plant, according to the present invention has a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, *Phythophthora* spp., *Cladosporium* spp., *Alternaria* spp., *Stemphylium* spp., thrips, *Pseudomonas* spp. Preferably the shaft length is at least 25 cm, more preferably at least 30 cm.

Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention has an erectness of the leaves of less than 50°, more preferably less than 45°, and even more preferably less than 40°. In a preferred embodiment, more than 80% of the leaves have an erectness of less than 50°, more preferably less than 45° and most preferably less than 40°. Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Preferably the bottom part of the shaft has a diameter that is less than 30% larger than the diameter of the upper part of the shaft, more preferably less than 20% larger than the upper part of the shaft, and most preferably less than 15% larger than the upper part of the shaft.

In another embodiment the present invention is directed to a method of producing a nuclear encoded dominant male sterile leek line comprising
 (a) Providing a first leek plant that is nuclear encoded dominant male sterile
 (b) Providing a second leek plant that is male fertile
 (c) Crossing the first and second leek plant to produce offspring
 (d) Selecting nuclear encoded dominant male sterile leek plants from the offspring of step (c) by marker assisted selection by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148.
 (e) Backcrossing nuclear encoded dominant male sterile leek plants selected from the offspring in step (d) with the second fertile leek plant.
 (f) repeating step (d) and (e) at least 2 times until a stable nuclear encoded dominant male sterile leek line is obtained.

Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

Preferably in the method of producing a nuclear encoded dominant male sterile leek line the first leek plant that is nuclear encoded dominant male sterile is obtainable from seed as deposited at the NCIMB with deposit number NCIMB 41699. Preferably, in the method according to the present invention in the offspring about 10% to about 80% of the leek plants is male sterile, preferably about 30% to about 60%, or more preferably about 40% to about 50%. Preferably, the first leek plant that is nuclear encoded dominant male sterile or the stable nuclear encoded dominant male sterile leek line is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably, the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

In a preferred method the first leek plant that is nuclear encoded dominant male sterile or the stable nuclear encoded dominant male sterile leek line has a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, thrips *Phythophthora* spp., *Cladosporium* spp., *Alternaria* spp., *Stemphylium* spp., *Pseudomonas* spp.

In another preferred embodiment the shaft length is at least 25 cm, more preferably at least 30 cm.

Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention has an erectness of the leaves of less than 50°, more preferably less than 45°, and even more preferably less than 40°. In a preferred embodiment, more than 80% of the leaves have an erectness of less than 50°, more preferably less than 45° and most preferably less than 40°. Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Preferably the bottom part of the shaft has a diameter that is less than 30% larger than the diameter of the upper part of the shaft, more preferably less than 20% larger than the upper part of the shaft, and most preferably less than 15% larger than the upper part of the shaft.

In a preferred method the first leek plant that is nuclear encoded dominant male sterile or the stable nuclear encoded dominant male sterile leek line is propagated vegetatively.

Nuclear encoded dominant male sterile leek plant according to the present invention is suitably propagated vegetatively. Plants may be regenerated from cells or tissue or organs of leek through various procedures including but not limited to doubled haploidisation, somatic hybridization, protoplast fusion, genetic transformation, vegetative propagation using leek cells, pollen, protoplasts, suspension cultures, callus, basal plates, flower heads, ovules, (somatic) embryos, leaves, roots and other plant parts using previously described methods.

In addition, the present invention is directed to genetic markers linked to dominant male sterility in leek characterized by a nucleic acid sequence selected from the group comprising SEQ ID NO 1-6, or AFLP marker selected from the group comprising P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

The present invention is also directed to the use of genetic markers according to the invention to select for a nuclear encoded dominant male sterile leek plant or seed or a nuclear encoded dominant male sterility trait in a leek plant or seed by marker assisted selection.

Furthermore, the present invention is directed to a method of selecting a nuclear encoded dominant male sterile leek plant or seed comprising
  (a) Isolating DNA from leek plant or seed
  (b) Using genetic marker according to the present invention
  (c) Identifying DNA wherein at least one of the genetic markers according to step (b) is present.
  (d) Identifying leek plant or seed from which selected DNA in step c) was isolated in step a).

Isolating DNA from seed and plants can be done in a destructive way and non-destructive way. In a preferred method the DNA is isolated in a non-destructive way such that the plant may grow further and be harvested and the seed may be used for germination and growing of plants. DNA may be isolated from plant parts, such as root, stem, leave, flower, pollen, anther, or any other part that will not destroy the plant when taken for isolation. Isolating DNA from seed may done from the seed coat or any other way that will not destroy the seed, see e.g. Meng L, and Feldman L. (2010) and Maoteng L, et al (2007).

The present invention is also directed to nuclear encoded dominant male sterile leek plant or seed obtainable from the method for selecting a nuclear encoded dominant male sterile leek plant or seed.

The present invention is furthermore directed to male sterile leek seed wherein the male sterility is dominant and nuclear encoded. Preferably the male sterile leek seed is seed as deposited at the NCIMB with deposit number NCIMB 41699. 61 In a preferred embodiment the male sterile leek seed has offspring wherein the about 10% to about 80% of the leek seed is male sterile, preferably about 30% to about 60%, or more preferably about 40% to about 50%.

In a preferred embodiment the male sterile leek seed according to invention is characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148. Preferably, the genetic marker is selected from the group consisting of SEQ ID 1, 4, 5 and 6, or at least one of the markers selected from the group consisting of AFLP markers P11/M85-362, P14/M40-267, P16/M85-218, P17/M89-288, P17/M33-228, P14/M65-119, P17/M40-369, P17/M86-274, and P16/M90-179.

In addition, homologues of SEQ ID NO 1-6 may also be used. Preferably the homologues are at least 70%, more preferably at least 80% and most preferably at least 90%, 95% or even 98% homologous. Preferably the homologues contain no more than 10 nucleotides mismatch, more preferably no more than 7 nucleotides mismatch, even more preferably no more than 5 nucleotides mismatch. Most preferably no more than 2 nucleotides mismatch.

In a preferred embodiment the male sterile leek seed according to the invention has a desirable phenotypic trait selected from the group consisting of dark green to blue-green color of the leaves, erectness of less than 90°, bolting less than 2%, flags less than 2%, no bulbing of the shaft, shaft length at least 20 cm, shaft diameter, at least 2.5 cm, no delaminating of the leaf after cutting, moderate to high resistance to diseases and pests selecting from the group consisting of rust, *Phythophthora* spp., *Cladosporium* spp., *Alternaria* spp., *Stemphylium* spp., thrips, *Pseudomonas* spp.

In another preferred embodiment the shaft length is at least 25 cm, more preferably at least 30 cm.

Preferably more than 70% of the leaves have an erectness of less than 90°. More preferably more than 80%, even more preferably more than 90% or 95%, and even more preferred more than 98% and most preferred all the leaves have an erectness of less than 90°. Preferably more than 70% of the leaves of the leek of the present invention have an erectness of the leaves of less than 50°, more preferably less than 45°, and even more preferably less than 40°. In a preferred embodiment, more than 80% of the leaves have an erectness of less than 50°, more preferably less than 45° and most preferably less than 40°.

Preferably more than 85% of the leaves have an erectness of less than 50°, more preferably less than 45° and most preferably less than 40°. More preferably, more than 90% of the leaves have an erectness of less than 50°, more preferably less than 45° and most preferably less than 40°. Most preferably more than 95% of the leaves have an erectness of less than 50°, more preferably less than 45° and most preferably less than 40°.

Preferably the bottom part of the shaft has a diameter that is less than 30% larger than the diameter of the upper part of the shaft, more preferably less than 20% larger than the upper part of the shaft, and most preferably less than 15% larger than the upper part of the shaft.

In a preferred embodiment the male sterile leek seed according to the invention wherein at least a part of the nuclear encoded dominant male sterile leek seed is propagated vegetatively.

The present invention is also directed to seed obtainable from plants according to invention.

Furthermore, the present invention is directed to a method according to the invention wherein the first leek plant is a leek plant according to the invention.

Nuclear encoded dominant male sterile leek plant according to the present invention are suitably propagated vegetatively. Plants may be regenerated from cells or tissue or organs of leek through various procedures including but not limited to doubled haploidisation, somatic hybridization, protoplast fusion, genetic transformation, vegetative propagation using leek cells, pollen, protoplasts, suspension cultures, callus, basal plates, flower heads, ovules, (somatic) embryos, leaves, roots and other plant parts using previously described methods.

REFERENCES

Allard, R. W. (1960) *Principles of Plant Breeding*
Mark J. Basset, (1986, editor), *Plant Breeding Perspectives*
Berninger, E. & Buret, P. 1967. Etudes des deficients chlorophylliens chez deux especes cultivees du genre *Allium*: l'oignon *A. cepa* 1. et le poireau *A. porrum* 1. Ann. Amelior. Plantes 17:175-194
Briggs, F. N. & Knowles, P. F., 1967. Introduction to Plant Breeding, Ch 21, p 265-280.
Buiteveld, J. 1998. Regeneration and interspecific somatic hybridisation in *Allium* for transfer of cytoplasmatic male sterility to leek. PhD thesis Wageningen Agric Univ
Buiteveld, J., Valk van der, P., Jansen, J., Creemers-Molenaar, J., Colijn-Hooymans, C. M. (1993). Callus induction and plant regeneration from explants of commercial cultivars of leek (*Allium ampeloprasum* var. *porrum* L.). Plant Cell Reports 12: 431-434.
Buiteveld, J.; Suo, Y, Lookeren Campagne van MM, Creemers-Molenaar J (1998) Production and characterization of somatic hybrid plants between leek (*Allium ampeloprasum* L.) and onion (*Allium cepa* L.) Theoretical and Applied Genetics 96, 765-775.
Curah L. (1986) Leek breeding: a review. J Hort Sc 61: 407-415
Dijcks, M., Van Lier, S. & Peeters, R. 1994. Male sterile leek unequivocally distinguished. Prophyta 3 sep 94:22-23
Dore, C. & Schweisguth, B 1980. [Vegetative propagation of leek for seed production] Eucarpia sect. Legumes, Versailles, 1980
Fehr, (1987) *Principles of Cultivar Development Theory and Technique*),
Havey, M. J., Leite, D. L. 1999. Toward the identification of cytoplasmic male sterility in leek: evaluation of organellar DNA diversity among cultivated accessions of *Allium ampeloprasum*. Journal of the american societ 124:163-165
Lamers, A. 1996 Genetic male sterility. Hybrid leek marks great advance in breeding. Prophyta ann. 1996:48-51
Maoteng L, Jianmin L, Zhangyi, Pei W, Lu G, Longjiang Y. Pak J. A simple DNA extraction method for PCR amplification from dry seeds of Brassica napus.
Biol Sci. 2007 Apr. 1; 10(7):1122-5.
Meer, Q. P. van der 1982 [Male sterility in leek] prophyta.
Meng L, Feldman L. A rapid TRIzol-based two-step method for DNA-free RNA extraction from Arabidopsis siliques and dry seeds. Biotechnol J. 2010 February; 5(2):183-6.
Michelmore R W, Paran I, Kesseli R V (1991) Identification of markers linked to disease-resistance genes by bulked segregant analysis: a rapid method to detect markers in specific genomic regions by using segregating populations. Proc Natl Acad Sci USA 88: 9828-9832
Novak F J (1986) *Allium*. In: Evans DA Handbook of plant cell culture 4, New York, pp 419-456
Peterka, H. & Budahn, H. 1996 [Interspecific crosses between onion (*Allium cepa*) and leek (A. ampeloprasum)] Vortr. Pflanzenzuchtg. 32:160-162
Peterka, H.; Budahn, H.; Schrader, O. 1997 Interspecific hybrids between onion (*Allium cepa* L) with S-cytoplasm and leek (*Allium ampeloprasum* l) Theoretical and applied genetics 94:383-389.
Peterka, H.; Budahn, H.; Schrader, O.; Havey, M. J. 2002 Transfer of a male-sterility-inducing cytoplasm from onion to leek (*Allium ampeloprasum* l) theoretical and applied geneti 105:173-181
Schavemaker C M, Jacobsen E (1995) Development of a cyclic somatic embryogenesis regeneration system for leek (*Allium ampeloprasum* L.) using zygotic embryos. Plant Cell Reports 14: 227-231.

Schweisguth, B. 1970 Preliminary studies for the improvement of leek *Allium porrum* l. Proposal for a breeding method. Ann. Amelior. Plantes 20:215-231

Schweisguth, B. 1972 Note sur la multiplication vegetative du poireau. Ann. Amelior. Plantes 22:127-131

Schweisguth, B. 1973 [Study on the heritability of three quantitative traits in leek (*Allium porrum* l.)] Ann. Amelior. Plantes 23:45-57

Schweisguth, B., 1986 O. Konvicka. Ed Which varietal structure for leek? *Allium* conference 1983 p 264-280

Shimasue, Y., ishizuka, K. & fukuda, M. 1990 Method of producing hybrid *Allium* plant and hybrid plant obtained thereby. European patent application 90103547.7

Silvertand, B. 1996 PhD Induction, maintenance and utilization of male sterility in leek (*Allium ampeloprasum* l.) thesis Wageningen Agric Univ isbn 90-5485-512-6; 144 pp Silvertand, B C H J. & van Harten, A M. 1992. The use of male sterility in breeding of leek (*Allium ampeloprasum* l.); prospects and problems. 13th Eucarpia conf. Angers, France, 1992:121-122

Silvertand, B C H J, Mens, B A. & van Harten, A M. 1989 [Male sterility in leek (*Allium porrum* l.)] Prophyta nr 10, 1989:289-292

Simmonds, N. W. (1979) *Principles of Crop Improvement;*

Smith, B. M.; Crowther, T. C. 1995 Inbreeding depression and single cross hybrids in leeks (*Allium ampeloprasum* ssp *porrum*). Euphytica 86:87-94

Vos P, Hogers R, Bleeker M, et al. (November 1995). "AFLP: a new technique for DNA fingerprinting". *Nucleic Acids Res.* 23 (21): 4407-14

Zabeau, M and P. Vos. 1993. Selective restriction fragment amplification: a general method for DNA fingerprinting. EP 0 534 858 A1

EXPERIMENTAL SECTION

Example 1

Making of Leek Plant and Leek Seed NCIMB 41699

Seeds from leek cultivar Porino were treated with a mutagenic solution NMU (N-nitroso-N-methylurea, 12.5 nM) and soaked for 0.5 hour. Plants obtained from these seeds were pollinated and a half-sib family plant was selected. Seeds from this half-sib family were sown and a sterile plant was selected. The selected plant was crossed with a pollinator and plants obtained there from were designated S-1001 and seeds are deposited under number NCIMB 41699 at NCIMB Ltd., Aberdeen. Two basal bulbs (little bulbs formed at the roots) were harvested to maintain the plant. Upon cross-breeding with other leek plants a high segregation for male sterility in the F1 was found (table 1). Phenotyping is done by observation of pollen, when pollen are observed the plant is designated as fertile.

TABLE 1 crosses of S-1001 with genetically distinct pollinators

| pollinator | Total # plants | % sterile | # fertile | # sterile |
|---|---|---|---|---|
| A | 21 | 43 | 12 | 9 |
| B | 26 | 54 | 12 | 14 |
| Total | 47 | 49 | 24 | 23 |

At another occasion, more crossing were made with S-1001 with genetically distinct pollinators (table 2)

TABLE 2 crosses of S-1001 with genetically distinct pollinators

| pollinator | Total # plants | % sterile | # fertile | # sterile |
|---|---|---|---|---|
| C | 24 | 50 | 12 | 12 |
| D | 27 | 67 | 9 | 18 |
| E | 34 | 38 | 21 | 13 |
| F | 32 | 59 | 13 | 19 |
| G | 35 | 34 | 23 | 12 |
| H | 49 | 41 | 29 | 20 |
| I | 24 | 46 | 13 | 11 |
| J | 27 | 63 | 10 | 17 |
| K | 34 | 64 | 12 | 22 |
| L | 20 | 55 | 9 | 11 |
| M | 31 | 45 | 17 | 14 |
| Total/avarage | 337 | 50 | 168 | 169 |

As can be seen, an average of about 50% male sterile plants in the F1 is obtained.

Example 2

Genetic Linkage of Nuclear Encoded Dominant Male Sterile Trait

The sterile line S-1001 was crossed with genetically distinct fertile pollinators to obtain different populations. These subpopulations were used to identify AFLP markers linked to the nuclear encoded dominant genetic male sterility (NMS) gene in leek. 375 individuals from 8 sub-populations were phenotyped, by absence or presence of pollen as described above. 81 sterile plants and 294 fertile plants were used.

Genomic plant DNA was digested with the restriction enzymes PstI and MseI. Then ligation is performed with two double stranded adapters:

```
alpha:
5'-CTCGTAGACTGCGTACATGCA-3'      (SEQ ID NO 20)

3'-CATCTGACGCATGT-5'             (SEQ ID NO 22)

beta
5'-GACGATGAGTCCTGAG-3'           (SEQ ID NO 21)

3'-TACTCAGGACTCAT-5'             (SEQ ID NO 23)
```

A PCR amplification is carried out on the restriction fragments ligated to the adapters with selected primers. The PCR produces a fragment with a specific size. More information on AFLP markers can be found in EP0534858 from Keygene. (Vos et al, 1995).

A Bulked Segregant Analysis (BSA) strategy (Michelmore et al., 1991) was carried out on individuals from two sub-populations (1 and 2). Individuals from the remaining 6 sub-populations (3-8) were used for verification of the closest linked marker.

One fertile and one sterile pool (F1 & S1) was used for the first BSA. This resulted in 4 candidate markers linked to sterility and 10 markers linked to fertility. The second BSA was performed using two other fertile and sterile pools (F2 & S2), which resulted in another 30 candidate markers linked to sterility. All markers were verified on two different fertile and sterile pools (F3 & S3) and (F4 & S4). After this verification it was found that marker P14/M65-119 is linked to the NMS gene.

Example 3

Testing of Predictive Value of AFLP Marker P14/M65-119

The AFLP marker P14/M65-119 was screened on DNA extracted from 173 individuals derived from 18 different subpopulations (different from the pools used for the BSA analysis) (Table 3) to assess the predictive value of this marker.

TABLE 3

Populations used to verify marker P14/M65-119 with percentage of observed correlation between phenotype and genotype (AFLP marker).

| subpopulation | Nr of plants | Phenotype = genotype | Recombination or mismatch | % correlation genotype-phenotype |
|---|---|---|---|---|
| 1 | 10 | 10 | 0 | 100% |
| 2 | 9 | 8 | 1 | 89% |
| 3 | 10 | 9 | 1 | 90% |
| 4 | 8 | 8 | 0 | 100% |
| 5 | 10 | 9 | 1 | 90% |
| 6 | 10 | 6 | 4 | 60% |
| 7 | 10 | 10 | 0 | 100% |
| 8 | 10 | 10 | 0 | 100% |
| 9 | 11 | 11 | 0 | 100% |
| 10 | 9 | 9 | 0 | 100% |
| 11 | 10 | 10 | 0 | 100% |
| 12 | 10 | 9 | 1 | 90% |
| 13 | 10 | 8 | 2 | 80% |
| 14 | 10 | 8 | 2 | 80% |
| 15 | 10 | 10 | 0 | 100% |
| 16 | 8 | 7 | 1 | 88% |
| 17 | 10 | 10 | 0 | 100% |
| 18 | 8 | 8 | 0 | 100% |
| | 173 | 160 | 13 | |
| | linkage | 92.5% | 7.5% | |

Results show that overall the predictive value of marker P14/M65-119 averages 92.5% for the phenotype (fertility or sterility) NEDMS. Ten populations had a 100% correlation, 5 showed around 90% correlation, 2 populations had an 80% correlation and one populations had only a 60% correlation between phenotype and marker genotype. Out of the total number of 173 only 13 plants the genotypic score did not correlate with the phenotype (7.5%). Mismatches can be due to multiple reasons among which are recombination events or miss-phenotyping.

Example 4

Other Markers Linked to Nuclear Encoded Dominant Male Sterility (NEDMS)

More AFLP markers linked to the NEDMS locus in leek were identified. Again a Bulked Segregant Analysis (BSA) strategy was carried out on individuals from one subpopulation and verified against individuals from other verification lines.

One fertile and one sterile pool (F5 & S5) was used for the first BSA. This resulted in the identification of 6 candidate markers linked to the nuclear encoded genetic male sterility (NEDMS) allele. After further verification on lines from another subpopulation (pool F6 & S6), two of these markers proved to be linked to the sterile phenotype. The second BSA was executed with the same fertile pool (F5) and another sterile individual (S6). Twelve more candidate markers were found. After verification on lines from another subpopulation, four markers proved to be linked to the sterile phenotype. To further check these markers two additional pools generated out of the verification lines were used. A third BSA resulted in 24 candidate markers, which were subsequently verified on 4 additional pools. Of these markers, 15 additional markers proved to be linked to the phenotype.

In total 288 AFLP primer combinations (PCs) were screened, which resulted in the identification of a total of 42 candidate AFLP markers (with different sizes) linked to the NEDMS locus. After initial verification, 21 markers from 14 PCs proved to be linked to the phenotype. Of these markers, 15 markers from 12 PCs were tested on 47 selected individuals. One of the new markers was found not to be linked to the NEDMS region. Table 4 summarizes all the 15 AFLP markers found (14 new markers from example 4 and the one previously identified in example 2) found to be linked to the NEDMS gene.

TABLE 4

Overview of AFLP markers found to be linked to the nuclear encoded dominant male sterility locus.
Forward Primer 5'- -> -3':
GAC TGC GTA CAT GCA XXX
Reverse Primer 5'- -> -3':
GAT GAG TCC TGA GTA YYY Y

| To detect AFLP fragment | Forward Primer XXX | SEQ ID NO | Reverse Primer YYY Y | SEQ ID NO | Expected fragment size in # nucleotides |
|---|---|---|---|---|---|
| P17/M40-277 | GCG | 7 | AAG C | 11 | 277 |
| P14/M89-333 | GAT | 8 | ATG G | 12 | 333 |
| P17/M44-529 | GCG | 7 | AAT C | 13 | 529 |
| P11/M85-362 | GAA | 9 | ATC G | 14 | 362 |
| P14/M40-267 | GAT | 8 | AAG C | 11 | 267 |
| P16/M85-218 | GCC | 10 | ATC G | 14 | 218 |
| P17/M89-288 | GCG | 7 | ATG G | 12 | 288 |
| P17/M33-228 | GCG | 7 | AAA G | 15 | 228 |
| P14/M65-119 | GAT | 8 | AGA G | 16 | 119 |
| P17/M84-401 | GCG | 7 | ATC C | 17 | 401 |
| P17/M85-159 | GCG | 7 | ATC G | 14 | 159 |
| P17/M40-369 | GCG | 7 | AAG C | 11 | 369 |
| P17/M86-274 | GCG | 7 | ATC T | 18 | 274 |
| P16/M90-179 | GCC | 10 | ATG T | 19 | 179 |
| P17/M89-148 | GCG | 7 | ATG G | 12 | 148 |

The identified AFLP markers were checked for their predictive value as summarized in table 5.

TABLE 5

Recombination rates for markers linked to the NEDMS gene

| | Recombination rate for F1 individuals | Recombination rate for verification individuals | Total | % correct |
|---|---|---|---|---|
| P17/M40-277 | 10/22 | 11/24 | 21/46 | 54 |
| P14/M89-333 | 4/22 | 8/31 | 12/53 | 77 |
| P17/M44-529 | 5/22 | 6/24 | 11/46 | 76 |
| P11/M85-362 | 3/22 | 6/51 | 9/73 | 88 |
| P14/M40-267 | 3/22 | 5/30 | 8/52 | 85 |
| P16/M85-218 | 3/21 | 5/32 | 8/53 | 85 |
| P17/M89-288 | 3/22 | 6/24 | 9/46 | 80 |
| P17/M33-228 | 3/22 | 6/24 | 9/46 | 80 |
| P14/M65-119 | 3/22 | 8/51 | 11/73 | 85 |
| P17/M84-401 | 3/22 | 7/23 | 10/45 | 78 |
| P17/M85-159 | 3/22 | 7/24 | 10/46 | 78 |
| P17/M40-369 | 3/22 | 6/22 | 9/44 | 80 |
| P17/M86-274 | 3/21 | 5/22 | 8/43 | 81 |
| P16/M90-179 | 3/22 | 4/32 | 7/54 | 87 |
| P17/M89-148 | 3/22 | 10/24 | 13/46 | 72 |

Seven AFLP fragments were subjected to nucleotide sequencing: P14/M65-119, P17/M84-401, P17/M85-159, P17/M40-369, P17/M80-274, P16/M90-179 and P17/M89-148. These AFLP fragments are the bottom 7 of table 4. AFLP fragment designated P17/M89-148 could not be sequenced. The rest of the AFLP fragment were sequenced and are designated SEQ ID 1 to 6.

SEQ ID NO 1: P14/M65-119 93 bases
CTGCAGATGCGCTTACGAAAACGCCTTCTCATGGCCCAATGCTCCAACGG

CGATCCTATTTTCGTAAAACTTACCTCCATCGGCACCTCTTAA

SEQ ID NO 2: P17/M84-401 351 bases
AGGACGACGTTGTGGAGTCCGGACGATGCATTCTTGTGGGTGGTATCSAT

GGAGTTCGCGGTGATGGGATTCNNNNCGTGCATGTGCATGGATGTGCAC

TGATTGAGTTTCAGGTGGAGGGAAAACGTGAACATGGGAGCTTGGTACCA

TCGGAAGGGGTGTGTGTATTATCTGGGAAGGGACTGGTAAACACGGGTGT

ATGTTTGGAGGGTTGGCGTTGATGGAAGTGGCTGTGTTGGCATGGAAGTA

TGGCGGTGAGTGGAGATATGATTGCTGCGGGTGAGTATACTGNNAGGG

AGTCGGTTTGGTATAAACAAAGGAANNAAGGACTAACGAAGATAAGGGAT

TAA

SEQ ID NO 3: P17/M85-159 136 bases
CTGCAGCGCCTNNNCGGTGAACGCCATGGTGGCTTCAGAGCTTACAAGG

GGCTACGACGTCGAACATGGTCGCAAGCAGCTCGATTTGGTGGTGATTTT

GCTTTAGTGGTGGAGGAATGTCATTATTGTCGATTAA

SEQ ID NO 4: P17/M86-274 274 bases
CTGCAGCGATGNNNGAGCGCANGAGCCGTNGCGAGCTCCGGATGAGTGA

CGCAGTGCAGAAACTGATTTGGGGCAGATCGATTTGATTCGAAGAGGAAC

NNATGANCTGGNTGNCGCGANCTTNTGGNTNTCTGGNTGGGGTATGCCA

NGCGNGNCGGNCTGTGGCTTTCGCGGCTGATGGANGGCGCTANNCGNA

GGANGNGCNGGTGGATTTTCNCTAGAGGCGGTGCTNTTTTGGCTGAAGC

CATTTTTGACNATTTTGGGGGAAGATTAA

SEQ ID NO 5: P17/M40-369 343 bases
CTGCAGCGTTGGGTGCATGGTTGGCGATAGGAGTGGGGTATGGTGTTCAC

GACAATGGAGTTGCTGTTATGGGACTGGGAGGTGAACAGGCCGCATGGTA

CTGTGCATTTGCGAAACAATGAAGGTAATGGGCTGTTTCTTTTTTTCTGG

AACATATTACTTGCGTTGGTGACAGAAGTTGTTTTACTGAGGGTGATCAC

GAGGGGAAGAGGATGCGAGGTGGAGCTGAGTAGTAGCAAGTGGACGGTAT

GGTTCAGACGGGAAGAAAACAACATAAATAGAGAAGAGAAATAAGGAAGA

TGGGCTAGAATTTTCATAAGGGGCCTGGGCCTAAGCGCTTTAA

SEQ ID NO 6: P16/M90-179 154 bases
TGCAGCCAATAGTCGAGCAGCTTCCTTCCACCGTTCCCCTCATCAAGGCA

CTACCACACATTGCCAACATCCTAACCACTCAGTGATCACCGCCGCATGT

CCTTCGCAGACCCCCTTACCCCTATAGTAAACTAAACATGCCACTCCACA

TTAA

SEQ ID NO 7:
GACTGCGTACATGCAGCG

SEQ ID NO 8:
GACTGCGTACATGCAGAT

SEQ ID NO 9:
GACTGCGTACATGCAGAA

SEQ ID NO 10:
GACTGCGTACATGCAGCC

SEQ ID NO 11:
GATGAGTCCTGAGTAAAGC

SEQ ID NO 12:
GATGAGTCCTGAGTAATGG

SEQ ID NO 13:
GATGAGTCCTGAGTAAATC

SEQ ID NO 14:
GATGAGTCCTGAGTAATCG

SEQ ID NO 15:
GATGAGTCCTGAGTAAAAG

SEQ ID NO 16:
GATGAGTCCTGAGTAAGAG

SEQ ID NO 17:
GATGAGTCCTGAGTAATCC

SEQ ID NO 18:
GATGAGTCCTGAGTAATCT

SEQ ID NO 19:
GATGAGTCCTGAGTAATGT

SEQ ID NO 20:
CTCGTAGACTGCGTACATGCA

SEQ ID NO 21:
GACGATGAGTCCTGA

SEQ ID NO 22:
TGTACGCAGTCTAC

SEQ ID NO 23:
TACTCAGGACTCAT

The invention claimed is:

1. Male sterile leek plant comprising an introgression from a leek plant from which seed is deposited at the National Collection of Industrial Food and Marine Bacteria in Aberdeen with deposit number NCIMB 41699, said introgression characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148, wherein the male sterility is dominant and nuclear encoded.

2. A method of producing a hybrid leek plant seed that is nuclear encoded male sterile comprising the steps of:
 a) providing a first leek plant that is nuclear encoded dominant male sterile, said plant being a leek plant from which seed is deposited at the National Collection of Industrial Food and Marine Bacteria in Aberdeen with deposit number NCIMB 41699, or said plant comprising an introgression from said leek plant from which seed is deposited at the National Collection of Industrial Food and Marine Bacteria in Aberdeen with deposit number NCIMB 41699, said introgression characterized by the presence of at least one of the genetic markers selected from the group consisting of SEQ ID 1-6 or at least one of the markers selected from the group consisting of AFLP markers P14/M65-119, P14/M89-333, P17/M44-529, P11/M85-362, P14/M40-267, P16/M85-218, P17/M89-288, P17/M33-228, P17/M40-277, P17/M84-401, P17/M85-159, P17/M40-369, P17/M86-274, P16/M90-179, and P17/M89-148;
 b) providing a second leek plant that is fertile;
 c) crossing the first and second leek plant; and
 d) producing seed therefrom which comprises the nuclear encoded male sterility.

3. A method to grow a nuclear encoded dominant male sterile leek plant by somatic reproduction from a tissue, cell or protoplast derived from a nuclear encoded dominant male sterile leek plant according to claim 1.

4. Nuclear encoded dominant male sterile seed or plant obtained by the method according to claim 2.

5. Nuclear encoded dominant male sterile leek plant obtained by growing the seed according to claim 4.

6. Plant part or a regenerable cell or protoplast derived from a nuclear encoded dominant male sterile leek plant according to claim 1, wherein the plant part is selected from the group consisting of leaf, pollen, ovule, embryo, root tip, anthers, flowers, seeds, seed coat, stem, bulbil, basal bulb or tissue of any thereof, and wherein the cell or protoplast regenerates to a leek plant being nuclear encoded dominant male sterile.

7. Plant part or a regenerable cell or protoplast, obtained from the plant produced by the method according to claim 2, wherein the plant part is selected from the group consisting of leaf, pollen, ovule, embryo, root tip, anthers, flowers, seeds, seed coat, stem, bulbil, basal bulb or tissue of any thereof, and wherein the cell or protoplast regenerates to a leek plant being nuclear encoded dominant male sterile.

8. Nuclear encoded dominant male sterile leek plant derived from the cell or protoplast or plant part according to claim 6.

9. Leek seed comprising a nuclear encoded dominant male sterility trait obtained from a leek plant according to claim 1.

10. The regenerable cell or protoplast according to claim 6, wherein the cell or protoplast is from a tissue selected from the group consisting of leaf, pollen, ovule, embryo, root tip, anthers, flowers, seeds, seed coat, stem, bulbil and basal bulb.

11. The regenerable cell or protoplast according to claim 7, wherein the cell or protoplast is from a tissue selected from the group consisting of leaf, pollen, ovule, embryo, root tip, anthers, flowers, seeds, seed coat, stem, bulbil and basal bulb.

* * * * *